(12) United States Patent
Hamaguchi et al.

(10) Patent No.: US 12,186,456 B2
(45) Date of Patent: Jan. 7, 2025

(54) ARTIFICIAL BONE AND MANUFACTURING METHOD OF ARTIFICIAL BONE

(71) Applicants: OSAKA UNIVERSITY, Suita (JP); Aimedic MMT CO., LTD., Tokyo (JP)

(72) Inventors: Satoshi Hamaguchi, Kyoto (JP); Tomoko Deguchi, Ibaraki (JP); Satoshi Sugimoto, Nara (JP); Takashi Kaito, Osaka (JP); Hideki Yoshikawa, Osaka (JP); Chieko Asamori, Hyogo (JP)

(73) Assignees: Osaka University, Osaka (JP); Aimedic MMT Co., Ltd., Tokyo (JP)

( * ) Notice: Subject to any disclaimer, the term of this patent is extended or adjusted under 35 U.S.C. 154(b) by 856 days.

(21) Appl. No.: 17/266,382

(22) PCT Filed: Aug. 5, 2019

(86) PCT No.: PCT/JP2019/030787
§ 371 (c)(1),
(2) Date: Feb. 5, 2021

(87) PCT Pub. No.: WO2020/031988
PCT Pub. Date: Feb. 13, 2020

(65) Prior Publication Data
US 2021/0290827 A1  Sep. 23, 2021

(30) Foreign Application Priority Data
Aug. 9, 2018  (JP) .................................. 2018-150717

(51) Int. Cl.
*A61L 27/56*  (2006.01)
*A61L 27/10*  (2006.01)
*A61L 27/34*  (2006.01)

(52) U.S. Cl.
CPC ............... *A61L 27/56* (2013.01); *A61L 27/10* (2013.01); *A61L 27/34* (2013.01); *A61L 2430/02* (2013.01)

(58) Field of Classification Search
CPC .......... A61L 27/56; A61L 27/10; A61L 27/34; A61L 2430/02
See application file for complete search history.

(56) References Cited

U.S. PATENT DOCUMENTS

| | | | |
|---|---|---|---|
| 2002/0052662 A1 | 5/2002 | Imura et al. | |
| 2003/0009225 A1* | 1/2003 | Khandkar | ............... A61L 27/56 623/17.16 |
| 2011/0311591 A1* | 12/2011 | Wang | ..................... A61P 31/10 424/94.63 |
| 2013/0095049 A1 | 4/2013 | Castro Feo et al. | |
| 2013/0108879 A1 | 5/2013 | Mochizuki et al. | |
| 2017/0020914 A1 | 1/2017 | Castro Feo et al. | |

FOREIGN PATENT DOCUMENTS

| | | | |
|---|---|---|---|
| JP | 2003-038636 A | 2/2003 | |
| JP | 2003038636 | * 2/2003 | |
| JP | 2004-159971 A | 6/2004 | |
| JP | 2011-045559 A | 3/2011 | |
| JP | 2012-012329 A | 1/2012 | |
| JP | 2012012329 | * 1/2012 | ............... A61K 6/58 |
| JP | 2014-004166 A | 1/2014 | |
| KR | 2013-0121812 A | 11/2013 | |

OTHER PUBLICATIONS

JP 2012012329 Machine Translation (Year: 2012).*
JP 2003038636 Machine Translation (Year: 2003).*
Office Action dated Jul. 5, 2022 issued over the corresponding Japanese Patent Application No. 2020-535774 with the English translation thereof.
Nishioka et al., "Immobilization of hydrophilic polymer on thin carbon coating surface by plasma treatment—post polymerization technique", Polymer preprints, Japan, 2007, vol. 56, No. 1 Disk1, p. 2117 (2PD182).
Hamawaki et al., "Chemical modification and characterization of functionalized DLC surfaces", Plasma science symposium/Symposium on plasma processing, 2008, vol. 25th, pp. 245-246.
Nakatani et al., "Surface Engineering by Plasma Techniques of DLC for Medical Materials and B lood-compatibility Evaluation", Journal of Photopolymer Science and Technology, 2008, vol. 21, No. 2, pp. 225-230.
Extended European search report dated Apr. 13, 2022 issued over the European Patent Application No. 19846595.7.
Moriguchi et al., "Impact of non-thermal plasma surface modification on porous calcium hydroxyapatite ceramics for bone regeneration", PLOS 1, vol. 13, No. 3, Mar. 14, 2018, pp. 1-18.
Myoui et al., "Special issue: Clinical application of biomaterial products from Japan, To regeneration for bone defect: Fine structure control of Artificial Bone", Journal of Japanese Society for Biomaterials, vol. 35, No. 2, pp. 98-105 (ISSN: 1347-71080) (p. 98, 2., fig. 1, pp. 98-99, 2.1., fig. 2), non-official translation.
Rubstein et al., "Osseointegration of porous titanium modified by diamond-like carbon and carbon nitride.", Diamond Related Materials, 2012, vol. 22, pp. 128-135.
Spraying technique, Jan. 2018, vol. 37, No. 3, p. 32-36 (ISSN : 0289-422 x) (pp. 34-35 4.1, 4.2), non-official translation (Nakatani, Tatsuyuki, medical field, Application of DLC coating technology to the medical field, Thermal Spraying Technology).

(Continued)

*Primary Examiner* — Sean M Basquill
(74) *Attorney, Agent, or Firm* — Carrier, Shende & Associates P.C.; Fulchand P. Shende; Joseph P. Carrier

(57) ABSTRACT

To provide an artificial bone having a porous structure with an improved affinity to osteogenic cells, an artificial bone (1) includes: a base material (2) containing porous ceramics provided with mutually interconnected multiple pores (6); a carbonaceous thin film (10) formed on an outer surface of the base material and wall surfaces (7) of the pores; and functional groups (13) including amino groups (12) provided on a surface and in an interior of the carbonaceous thin film.

8 Claims, 14 Drawing Sheets

(56) References Cited

OTHER PUBLICATIONS

PCT/ISA/237 from International Application PCT/JP2019/030787, English translation of the Written Opinion Of The International Searching Authority.
PCT/ISA/210 from International Application PCT/JP2019/030787 with the English translation thereof.
Office Action dated Dec. 7, 2021 issued over the corresponding Japanese Patent Application No. 2020-535774, with the English translation thereof.

* cited by examiner

*Fig.6*
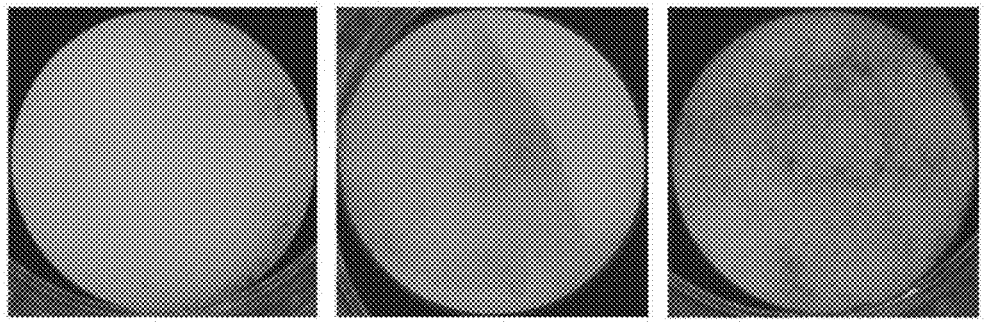
Comparative Example
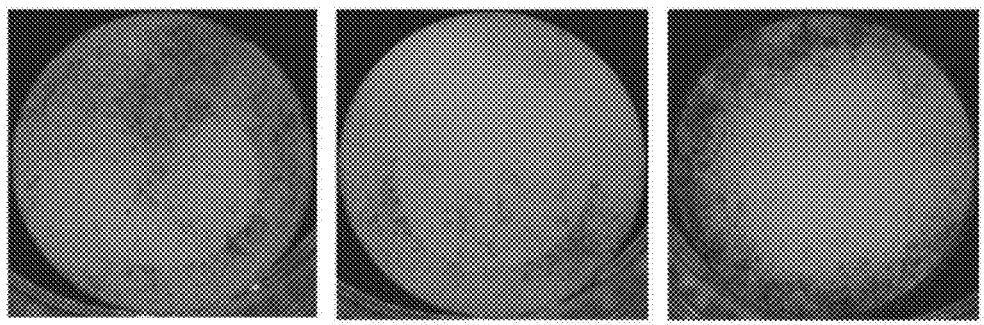
Example 2

Fig. 11
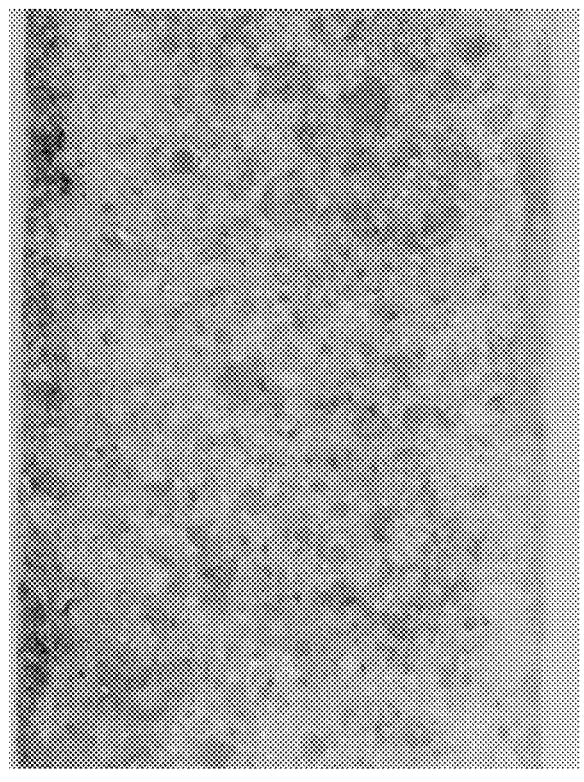
(B)
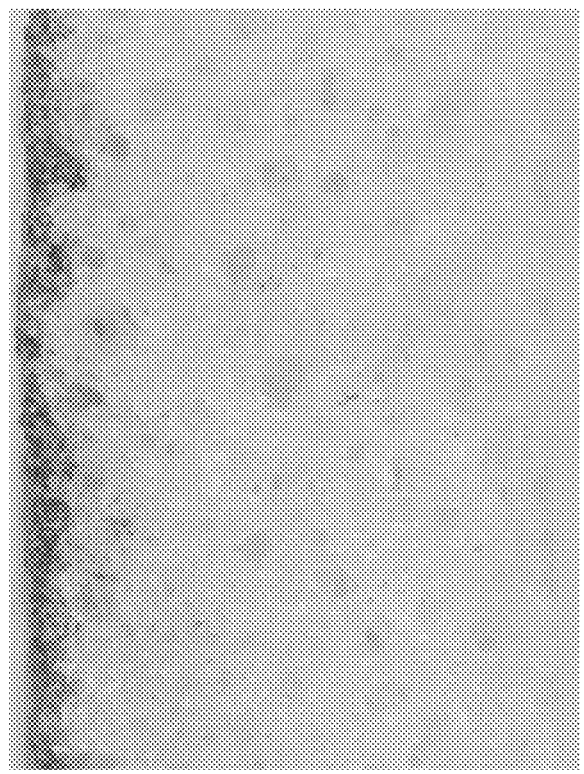
(A)
up ←→ down

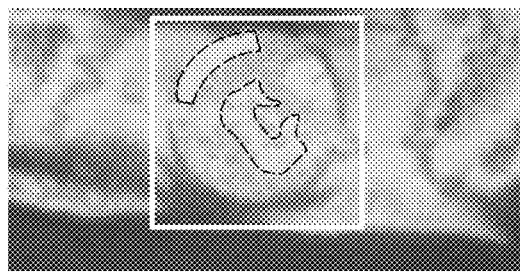
(D)
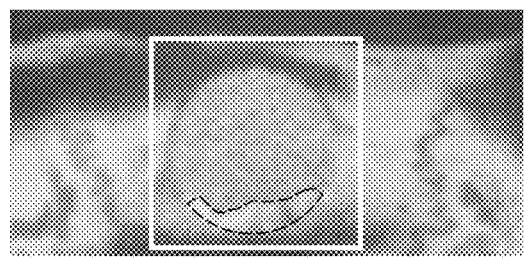
(B)
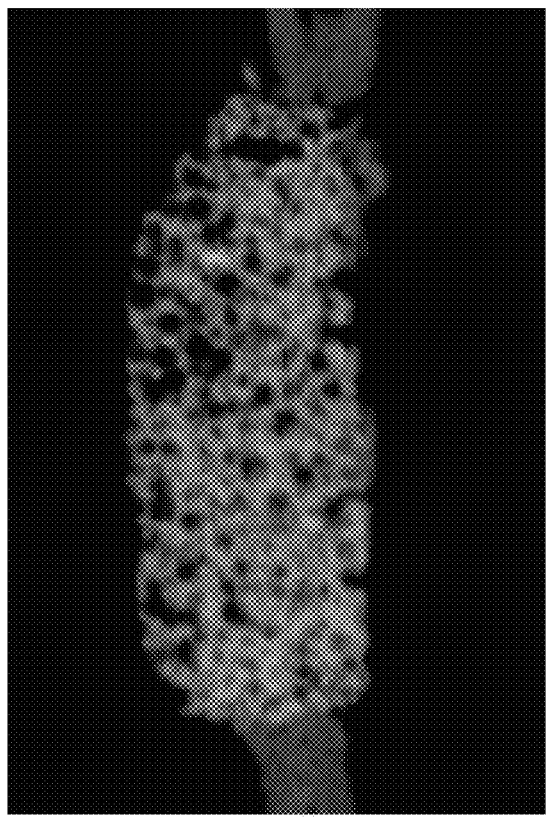
(C)
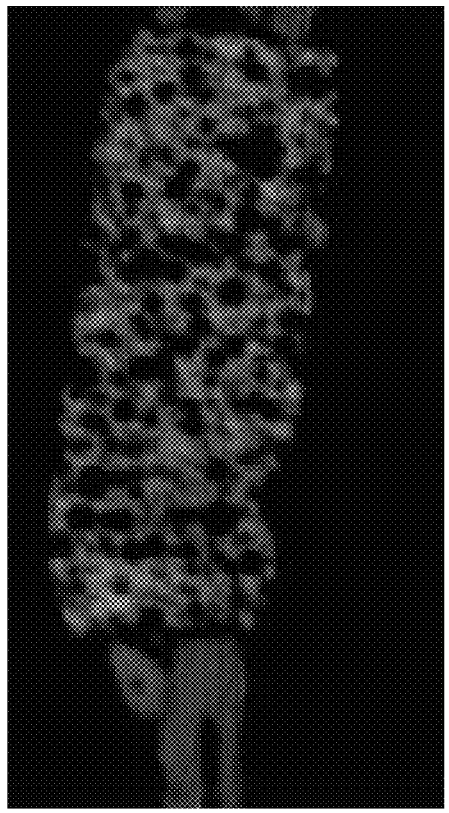
(A)
Fig. 13

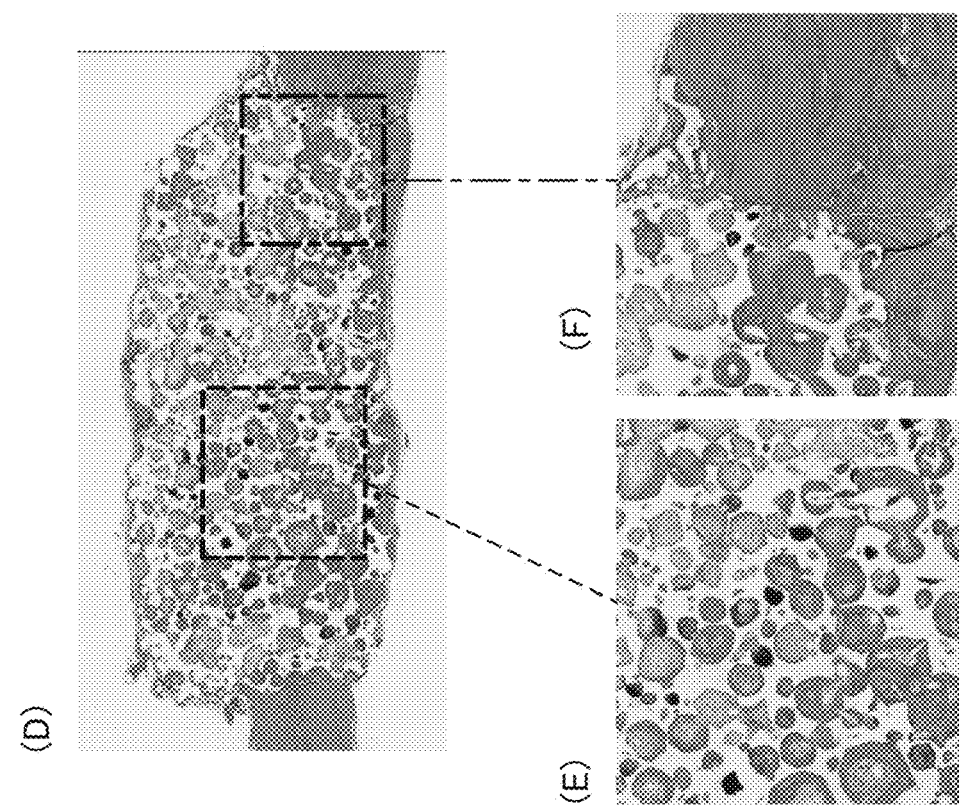
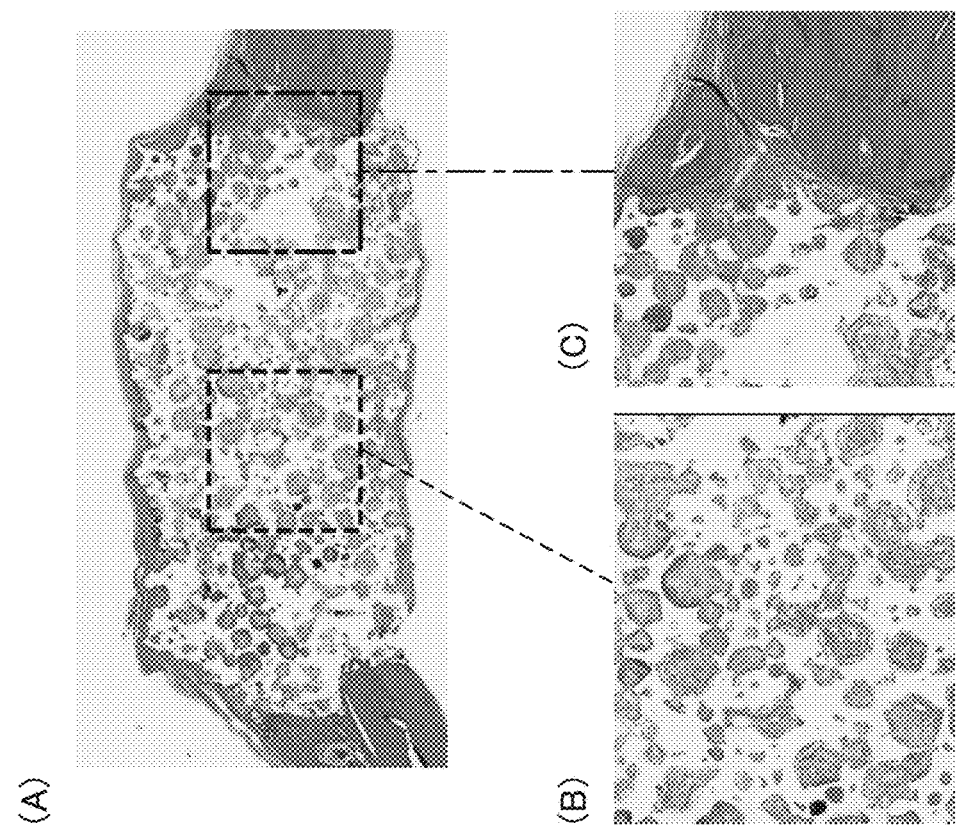
Fig.14

ARTIFICIAL BONE AND MANUFACTURING METHOD OF ARTIFICIAL BONE

TECHNICAL FIELD

The present disclosure relates to an artificial bone containing porous ceramics and a manufacturing method of the artificial bone.

BACKGROUND ART

Some known implant materials such as those for an artificial dental root or the like are provided with a carbonaceous thin film on a surface thereof (for example, Patent Document 1). In the implant material of Patent Document 1, the carbonaceous thin film contains functional groups containing oxygen (carboxylic groups) and functional groups containing nitrogen (amino groups). By controlling the ratio between the carboxylic groups and the amino groups to a prescribed value, it is possible to suppress differentiation to osteoclasts and to promote differentiation to osteoblasts.

An artificial bone having a porous structure is known (for example, Patent Document 2). In the artificial bone of Patent Document 2, osteogenic cells get into the pores, whereby the bone tissue formation is done at early stage.

PRIOR ART DOCUMENT(S)

Patent Document(s)

[Patent Document 1] JP2011-45559A
[Patent Document 2] JP2003-38636A

SUMMARY OF THE INVENTION

Task to be Accomplished by the Invention

In the artificial bone of Patent Document 1, the functional groups are provided on the surface of the carbonaceous thin film, and therefore, there is a problem that the affinity between the artificial bone and the osteogenic cells decreases if the surface of the carbonaceous thin film is eroded by the blood stream or the like.

In view of the foregoing background, an object of the present invention is to provide an artificial bone having a porous structure with an improved affinity to osteogenic cells.

Means to Accomplish the Task

To achieve the above object, one embodiment of the present invention provides an artificial bone (1) including: a base material (2) containing porous ceramics provided with mutually interconnected pores (6); a carbonaceous thin film (10) formed on an outer surface of the base material and wall surfaces (7) of the pores; and functional groups (13) including amino groups (12) provided on a surface and in an interior of the carbonaceous thin film.

According to this configuration, since the amino groups are provided on the surface and in the interior of the carbonaceous thin film, the amino groups provided in the interior of the carbonaceous thin film is exposed when the surface of the carbonaceous thin film is eroded by the blood stream or the like, and therefore, it is possible to prevent the decrease in the affinity between the artificial bone and the osteogenic cells due to the erosion of the surface of the carbonaceous thin film. In addition, since the carbonaceous film is formed on the wall surfaces of the pores and the amino groups are formed on the surface and in the interior of the carbonaceous film, the affinity between the artificial bone and the osteogenic cells can be improved in the interior of the base material as well.

In the above configuration, preferably, an abundance ratio of nitrogen on the surface and in the interior of the carbonaceous thin film is at least 3%.

According to this configuration, the carbonaceous thin film may be provided with sufficient amino groups to provide an affinity between the artificial bone and the osteogenic cells.

In the above configuration, preferably, the abundance ratio of nitrogen on the surface and in the interior of the carbonaceous thin film is at least 10%.

According to this configuration, the carbonaceous thin film may be provided with a more sufficient amount of amino groups required to improve the affinity between the artificial bone and the osteogenic cells.

In the above configuration, preferably, the pores are substantially spherical in shape and have an average diameter greater than or equal to 50 μm and less than or equal to 600 μm, and interpore connecting portions (8) each interconnecting two pores with each other are substantially circular in shape and have an average diameter greater than or equal to 5 μm.

According to this configuration, it is possible to have the osteogenic cells enter the interior of the base material, and in the manufacturing process, to form the carbonaceous thin film more on the wall surfaces of the pores in the interior of the base material.

In the above configuration, preferably, at least part of the carbonaceous thin film is formed on the wall surfaces of the pores (7) at a depth of 1 mm or more from the outer surface of the base material.

According to this configuration, the osteogenic cells can easily enter the interior of the base material, whereby the affinity between the artificial bone and the osteogenic cells can be improved further.

In the above configuration, preferably, the carbonaceous thin film is formed to reach the wall surfaces of the pores positioned in a central part of the base material.

According to this configuration, the affinity to the osteogenic cells can be improved over the entirety of the interior of the artificial bone so that the bone tissue formation can be accelerated.

In the above configuration, preferably, the carbonaceous thin film is a polymer film.

According to this configuration, it is possible to form the carbonaceous thin film without requiring a step of implanting high energy ions to harden the carbonaceous thin film, and therefore, the manufacturing process of the artificial bone can be simplified.

To achieve the above object, one embodiment of the present invention provides a manufacturing method of an artificial bone (1), the method comprising: a step of preparing a base material (2) containing porous ceramics provided with mutually interconnected pores (6); and a step of forming a carbonaceous thin film (10) on an outer surface of the base material and on wall surfaces (7) of the pores by a chemical vapor deposition method using plasma containing hydrocarbon, molecules containing nitrogen atoms, and inert gas.

According to this configuration, it is possible to form the carbonaceous thin film and at the same time to have amino groups attached to the carbonaceous thin film. Thus, it is possible to provide the amino groups on the surface and in the interior of the carbonaceous thin film. Thereby, even if the surface of the carbonaceous thin film is eroded, a state in which the amino groups are provided on the surface of the carbonaceous thin film is maintained. Therefore, it is possible to prevent the decrease in the affinity between the artificial bone and the osteogenic cells due to the erosion of the surface of the carbonaceous thin film, and the artificial bone having a high affinity to the osteogenic cells can be manufactured more simply.

Effect of the Invention

According to the foregoing configuration, it is possible to provide an artificial bone having a porous structure with an improved affinity to osteogenic cells.

BRIEF DESCRIPTION OF THE DRAWINGS

FIG. 6 shows photographs showing the results of ALP dyeing experiment (on the fourth day) of three base materials (upper row) and three samples of Example 2 (lower row);

FIG. 11 shows photographs of dyed sections of (A) the artificial bone of Example 2 and (B) the base material 2, after continuous culture of osteoblast-like cells;

FIG. 13 shows X-ray photographs of (A) a side of the base material transplanted in an SD rat, (B) a front of this base material, (C) a side of the artificial bone of Example 2 transplanted in an SD rat, and (D) a front of this artificial bone of Example 2; and FIG. 14 shows (A) a photograph of a dyed section of the base material transplanted in an SD rat, (B) an enlarged view of a part thereof surrounded by a broken line, (C) an enlarged view of a part thereof surrounded by a two-dot chain line, (D) a photograph of a dyed section of the artificial bone of Example 2 transplanted in an SD rat, (E) an enlarged view of a part thereof surrounded by a broken line, and (F) an enlarged view of a part thereof surrounded by a two-dot chain line.

MODES FOR CARRYING OUT THE INVENTION

In the following, an artificial bone according to the present invention will be described.

Figure 1:
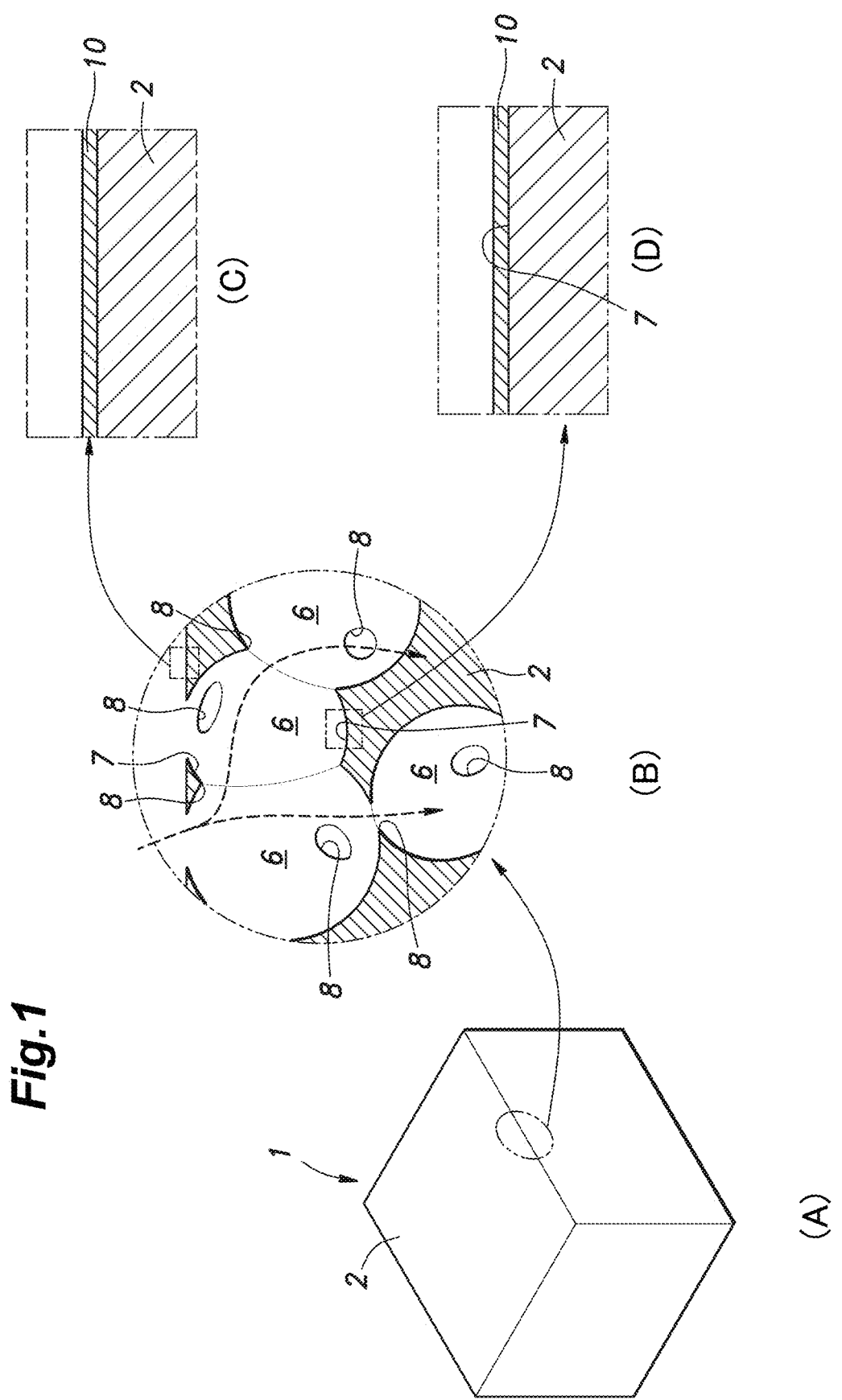
FIG. 1 shows (A) a schematic diagram of an artificial bone according to an embodiment, (B) a schematic diagram showing a pore portion of the artificial bone, (C) an enlarged view of a surface of the artificial bone, and (D) an enlarged view of the pore portion.

As shown in (A) of FIG. 1, an artificial bone 1 includes a base material 2 as a matrix thereof. The base material 2 contains porous ceramics as a main component. The porous ceramics is preferably made of hydroxyapatite, β-TCP (β-tricalcium phosphate) or a mixture of hydroxyapatite and β-TCP.

As shown in (B) of FIG. 1, in the present embodiment, the base material 2 has a substantially rectangular parallelepiped shape. The base material 2 has multiple pores 6 and forms a porous structure. Each pore 6 is defined by a pore wall surface 7 and has a substantially spherical shape. The average diameter of the pores 6 is greater than or equal to 50 μm and less than or equal to 600 μm, and preferably, greater than or equal to 80 μm and less than or equal to 300 μm. In the present embodiment, the average diameter of the pores 6 is 150 μm. The pores 6 are interconnected with each other via interpore connecting portions 8. Each interpore connecting portion 8 is substantially circular in shape. The average diameter of the interpore connecting portions 8 is greater than or equal to 5 μm, and more preferably, greater than or equal to 10 μm and less than or equal to 100 μm. In the present embodiment, the average diameter of the interpore connecting portions 8 is 40 μm. Note that the average diameter of the pores 6 is calculated by polishing the base material 2 embedded in resin, observing it with an electron microscope or the like to select substantially spherical pores 6 by means of image analysis, and measuring the pore area of them. Preferably, the pore area is calculated by measuring the pore areas of at least 300 pores 6 and averaging them. The pore area obtained here should preferably be three-dimensionally corrected because it is measured in a section by a plane passing a part of a substantially spherical pore 6 which may not coincide with the diameter of the pore 6. The average diameter of the interpore connecting portions 8 is preferably measured by using the well-known mercury intrusion porosimetry. In a case where the mercury intrusion porosimetry cannot be applied, one may observe the cross section of the base material 2 with an electron microscope, measure the diameters of the interpore connecting portions 8, and calculate the average thereof as the average diameter. Also preferably, the porosity of the base material 2 is greater than or equal to 60% and less than or equal to 90%, and the pore volume in which living body tissue can enter occupies 50%. Note that the porosity is preferably calculated by preparing a sintered body having the same composition as the base material 2, obtaining the true density ($\rho^*$) of the sintered body by using a true density meter, obtaining the density (ρ) of the base material 2 by dividing its weight by the volume obtained from the dimensions of the base material 2, and calculating the porosity as $1-\rho/\rho^*$.

As shown in (C) and (D) of FIG. 1, the outer surface of the base material 2 and the pore wall surfaces 7 are each provided with a carbonaceous thin film 10. At least part of the carbonaceous thin film 10 is formed to extend from the outer surface of the base material 2 (part of the surface defining the outer contour) to the pore wall surfaces 7 positioned at a prescribed depth (adsorption depth). The adsorption depth is at least 0.3 mm, and preferably is at least 1 mm. More preferably, the adsorption depth is greater than or equal to 2 mm. In the present embodiment, the adsorption depth is about 2 mm.

Also, the carbonaceous thin film 10 is preferably formed to reach the wall surfaces of the pores 6 positioned in a central part of the base material 2. Thereby, the carbonaceous thin film 10 is formed on the wall surfaces of the pores 6 (namely, the pore wall surfaces 7) positioned in the deepest part from the outer surface of the base material 2.

The depth here refers to a distance from a reference point positioned on an end (outer surface) of a sample. The reference point is determined by obtaining an approximate position of the end of the sample by using a camera, measuring XPS randomly at multiple points in the vicinity thereof, and thereafter determining, from among the multiple points, a point where the maximum XPS signal was obtained.

The carbonaceous thin film 10 preferably is a hydrocarbon polymer film having a thickness greater than or equal to 0.1 μm and less than or equal to 3.0 μm. The carbonaceous thin film 10 may be a diamond-like carbon (DLC) film.

Figure 2:
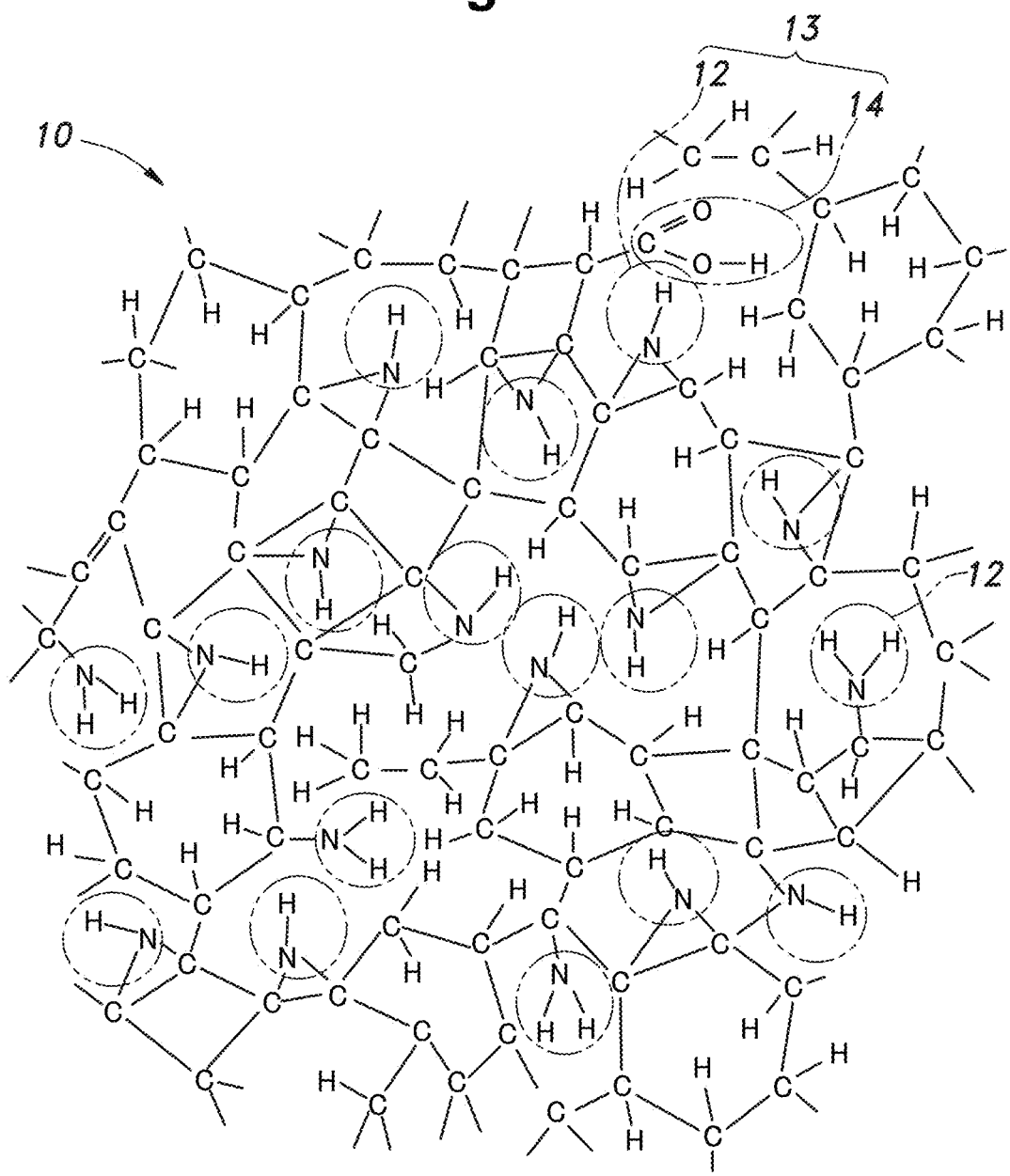
FIG. 2 is a schematic diagram of an interior of a carbonaceous thin film.

The carbonaceous thin film 10 is provided, on a surface and in an interior (see FIG. 2) thereof, with functional groups 13 (see the portion surrounded by a two-dot chain line in FIG. 2) including amino groups 12 (primary amine —$NH_2$, secondary amine —NH, or tertiary amine —N). The amino groups 12 are provided substantially uniformly in the interior of the carbonaceous thin film 10.

Note that in the present description, the primary amines, secondary amines, and tertiary amines are collectively referred to as amino groups. (More precisely, the amino groups 12 here refer to monovalent functional groups (—$NH_2$, —NHR, —NRR') (R is a hydrocarbon residue) obtained by removing hydrogen from ammonia, primary amines, or secondary amines. In the present description, a monovalent functional group (—$NH_2$) obtained by removing hydrogen from ammonia may be referred to as a primary amine, a monovalent functional group (—NH) obtained by removing hydrogen from a primary amine may be referred to as a secondary amine, and a monovalent functional group (—N) obtained by removing hydrogen from a secondary amine may be referred to as a tertiary amine, as necessary.)

The functional groups 13 may include carboxylic groups 14 (—COOH), where a carboxylic group is a functional group containing oxygen. To provide the carbonaceous thin film 10 with a sufficient amount of amino groups 12 required to improve the affinity between the artificial bone 1 and the osteogenic cells, the abundance ratio (atomic percent) of nitrogen on the surface and in the interior of the carbonaceous thin film 10 (the abundance ratio of nitrogen in the carbonaceous thin film 10 containing carbon, oxygen, etc.) is preferably greater than or equal to 3%, and more preferably is greater than or equal to 10%. Specifically, the abundance ratio of each element is determined based on the energy spectrum of photoelectrons obtained by using X-ray photoelectron spectroscopy (XPS), and corresponds to the ratio of the atoms of each element to the all atoms present in a sphere which has a center at the target point and whose diameter coincides with the spot diameter (about 2 mm to 1 cm) of the X-ray used in the XPS.

Figure 3:
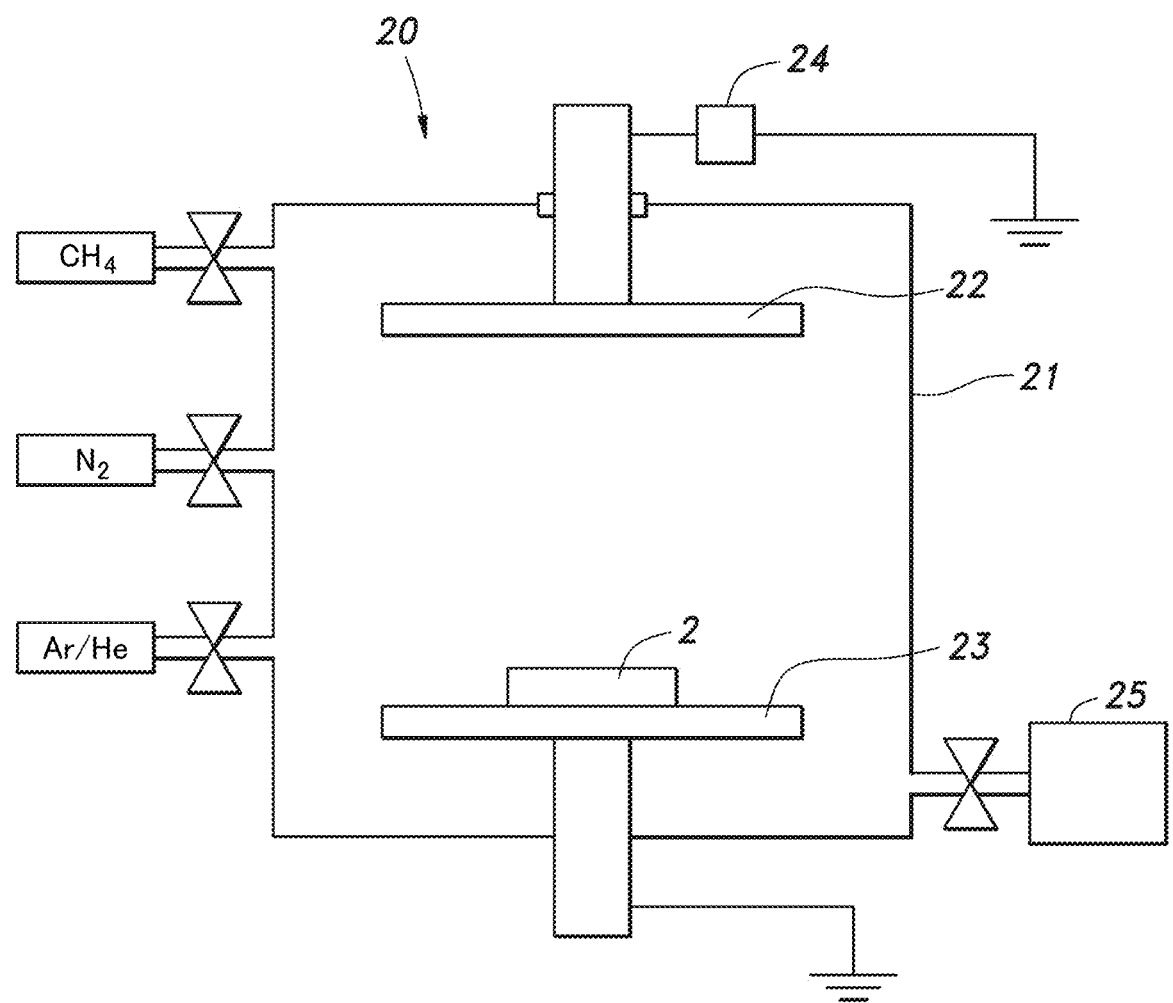
FIG. 3 is a schematic diagram of a plasma device used in the manufacture of the artificial bone according to the embodiment.

Next, a manufacturing method of the artificial bone 1 will be described. In the manufacture of the artificial bone 1, a plasma device 20 schematically shown in FIG. 3 is used. The plasma device 20 includes a vacuum chamber 21 (hereinafter, chamber), in which a pair of parallel plate electrodes 22, 23 separated vertically and having a disc-shape is provided. The lower plate electrode 22 is grounded and the upper plate electrode 23 is connected with a voltage generator 24. The chamber 21 is connected with a vacuum pump 25 for evacuating the interior of the chamber 21.

When manufacturing the artificial bone 1, first, the base material 2 is placed on the lower plate electrode 22, and the chamber 21 is vacuum-evacuated by the vacuum pump 25 to prepare for film formation (preparation step).

Next, while the interior of the chamber 21 is being evacuated, nitrogen, a hydrocarbon-containing gas, and an inert gas are introduced into the interior of the chamber 21 at respective constant flow rates. As the hydrocarbon-containing gas, methane gas is preferably used. In this way, by using hydrocarbon having a low molecular weight, it is possible to lower the molecular weight of hydrocarbon, and therefore, hydrocarbon can enter deeper from the outer surface of the base material 2 compared to when other hydrocarbon is used. As the inert gas, it is preferred to use helium gas or argon gas.

Next, a prescribed voltage is applied to the upper plate electrode 23 by the voltage generator 24 to generate plasma between the plate electrodes 22, 23. The plasma generating conditions may be known conditions; for example, the flow rate of nitrogen gas may be set at 5 sccm, the flow rate of methane gas may be set at 5 sccm, and the flow rate of helium gas or argon gas may be set at 5 sccm. For more details of the conditions for the plasma generation, reference should be made to "Moriguchi Y, Lee D-S, Chijimatsu R, Thamina K, Masuda K, Itsuki D, et al. (2018) Impact of non-thermal plasma surface modification on porous calcium hydroxyapatite ceramics for bone regeneration. PLoS ONE 13 (3): e0194303."

When the voltage is applied to the upper plate electrode 23, part of the nitrogen molecules and the hydrocarbon-containing gas in the chamber 21 are dissociated to become chemically active radicals. Further, due to collision with electrons accelerated by the electric field generated between the plate electrodes 22, 23, the electronic state of the molecules and radicals in the plasma may be excited so that they become chemically more active. The activated chemical species (molecules and radicals in the plasma) are adsorbed on the outer surface of the base material 2 and the pore wall surfaces 7 up to a prescribed depth from the outer surface of the base material 2 and form the carbonaceous thin film 10 (film forming step). Namely, in the film forming step, the carbonaceous thin film 10 is formed by so-called plasma CVD, which is one of chemical vapor deposition methods, using the plasma containing nitrogen, hydrocarbon (methane), and inert gas (helium or argon).

In the film forming step, since nitrogen is introduced at a constant flow rate, the carbonaceous thin film 10 is formed while being terminated by the amino groups 12. Thereby, the amino groups 12 are distributed substantially uniformly on the surface and in the interior of the carbonaceous thin film 10.

By continuing the film forming step for a prescribed time, the amino groups 12 are provided on the surface and in the interior of the carbonaceous thin film 10 formed on the outer surface of the base material 2 and the pore wall surfaces 7 up to a depth greater than or equal to 0.3 mm, more preferably greater than or equal to 1 mm, from the outer surface.

In this way, by providing the amino groups 12 on the surface and in the interior of the carbonaceous thin film 10 formed on the pore wall surfaces 7, the affinity between the pore wall surfaces 7 and the osteogenic cells is improved. Thereby, the osteogenic cells can enter the interior of the base material 2 easily, and the osteogenic cells are easily attached to the artificial bone 1 in the interior of the pores also.

The carbonaceous thin film 10 is preferably formed to reach the wall surfaces of the pores 6 positioned in the central part of the base material 2. More specifically, it is preferred that the carbonaceous thin film 10 reaches the wall surfaces of the pores 6 (the pore wall surfaces 7) positioned in the deepest part from the outer surface of the base material 2. Thereby, the carbonaceous thin film 10 is formed in the pores 6 formed in the interior of the artificial bone 1 at any depth. Therefore, even if the artificial bone 1 is eroded by the blood stream or the like, the affinity to the cells can be maintained, and the affinity to the osteogenic cells can be improved over the entire interior of the artificial bone 1.

Also, in the film forming step, the carbonaceous thin film 10 may be formed as a polymer film, and does not necessarily have to be formed as a diamond-like carbon film. Thereby, the carbonaceous thin film 10 can be formed by a more simple process without requiring a step of implanting high energy ions to harden the carbonaceous thin film 10 as when forming the diamond-like carbon.

After the film forming step is completed, the interior of the chamber 21 is evacuated. Thereafter, nitrogen, atmosphere or the like is introduced into the interior of the chamber 21 to vent the chamber 21, and the base material 2 is taken out (take-out step), whereby the manufacture of the artificial bone 1 is completed.

Next, effects of the artificial bone 1 according to the present invention will be described. By performing the above-described manufacturing process, an artificial bone 1 obtained by subjecting a base material 2 consisting of a porous hydroxyapatite to plasma irradiation for 30 minutes with introduced methane, nitrogen, and argon (Example 1), an artificial bone 1 obtained by subjecting a similar base material 2 to plasma irradiation for 30 minutes with introduced methane, nitrogen, and helium (Example 2), and an artificial bone 1 obtained by subjecting a similar base material 2 to plasma irradiation for 20 minutes with introduced methane, nitrogen, and helium (Example 3) were prepared. Note that in in Examples 1 to 3, the flow rate of methane, the flow rate of argon, and the flow rate of helium were set to be the same. The flow rate of the nitrogen gas in Example 1 was the same as the flow rate of the other gases, while in the film forming step in Examples 2 and 3, the flow rate of the nitrogen gas was doubled compared to the case of Example 1. In Example 2, the pressure in the chamber during plasma irradiation was set to 70% of that of Examples 1 and 3. Further, in the manufacture of the artificial bones 1 of Examples 1 to 3, cylindrical base materials 2 each having a radius of 5 mm and a thickness of 2 mm were used.

Figure 4:
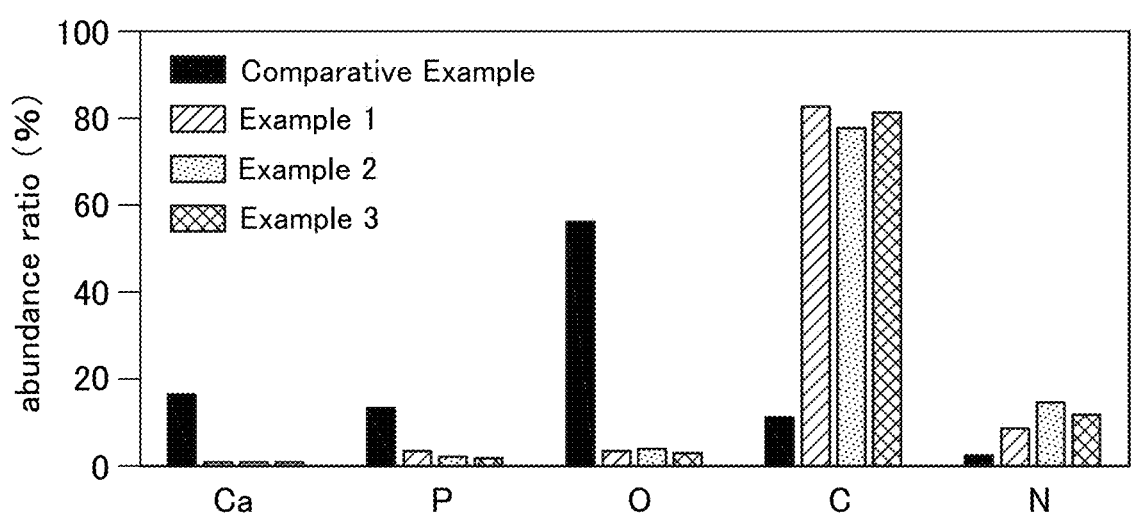
FIG. 4 is a graph showing abundance ratios of elements (calcium (Ca), phosphorus (P), oxygen (O), carbon (C), nitrogen (N)) on the surface of a base material (Comparative Example) and on the surface of the carbonaceous thin film on the surface of the artificial bone (Examples 1 to 3)

Subsequently, the abundance ratios (%) of calcium (Ca), phosphorus (P), oxygen (O), carbon (C), and nitrogen (N) on the surface of the base material 2 (Comparative Example) and on the surface of the carbonaceous thin film 10 provided on the outer surface of each of Examples 1 to 3 were measured by X-ray photoelectron spectroscopy (XPS), as shown in FIG. 4. More specifically, by using ESCA850M, which is an XPS device made by SHIMADZU CORPORATION, MgKα ray (1253.6 eV) was irradiate onto the surface of each sample, and an energy spectrum of generated photoelectrons was measured to calculate the abundance ratio (%) of each element. Note that since hydrogen cannot be detected by XPS, the abundance ratio of hydrogen is ignored in FIG. 4. Also, with ESCA850M, the spot diameter of X-ray was about 1 cm.

As shown in FIG. 4, the abundance ratios of phosphorus and oxygen are reduced in each of Examples 1 to 3 compared to Comparative Example. This indicates that since the surface of the base material 2 of each of Examples 1 to 3 was covered by the carbonaceous thin film 10, fewer photoelectrons were released from the atoms constituting the base material 2 (hydroxyapatite) serving as a foundation. Also, in each of Examples 1 to 3, the abundance ratios of carbon and nitrogen were increased compared to Comparative Example. This indicates that the carbonaceous thin film 10 formed on the surface of each of Examples 1 to 3 is provided with the amino groups 12.

In Example 2, Example 2, and Example 3, since the abundance ratio of oxygen is low compared to the abundance ratio of nitrogen, it is inferred that on the surface of the carbonaceous thin film 10, the carboxylic groups 14 are smaller in number compared to the amino groups 12.

Figure 5:
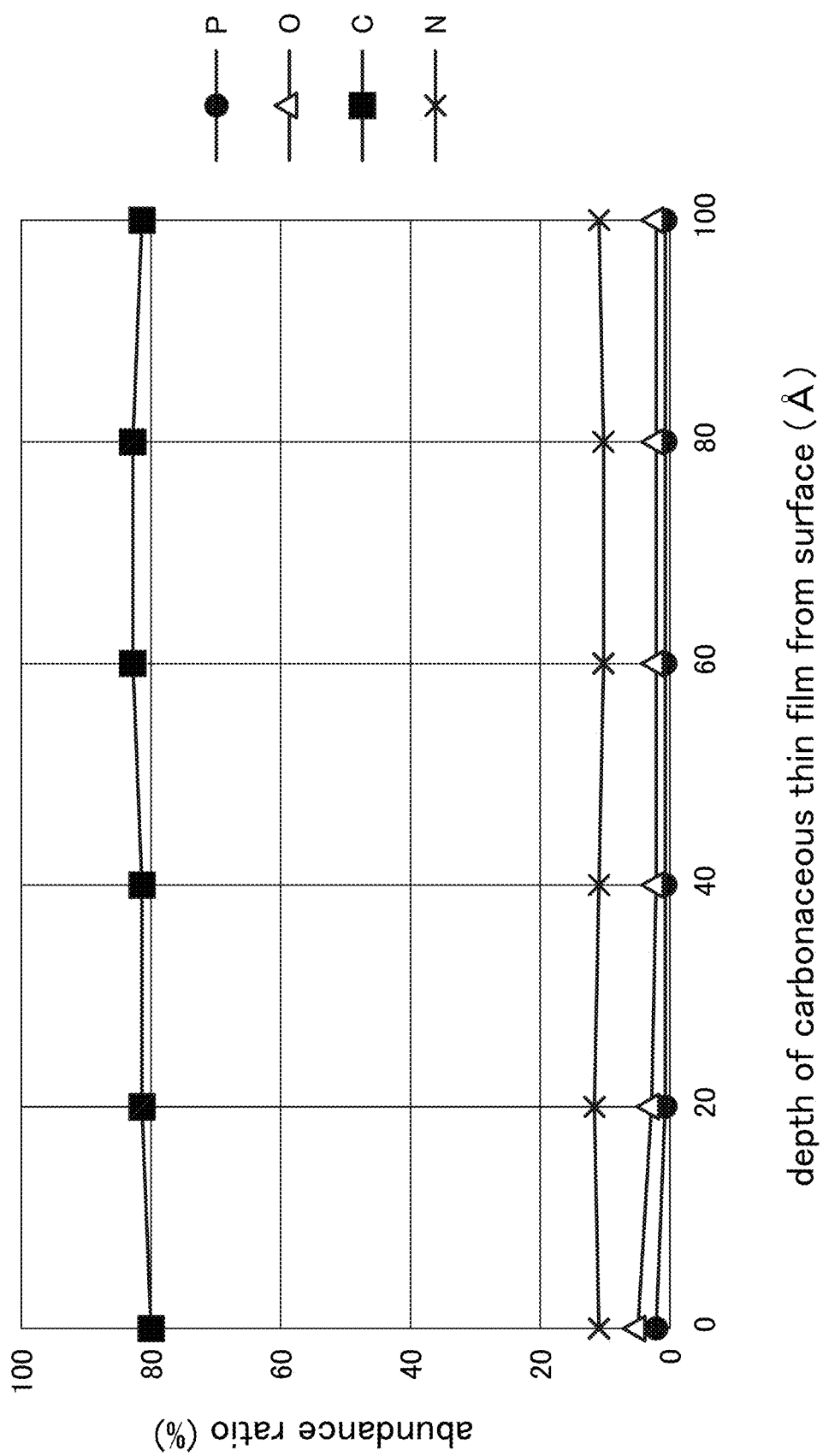
FIG. 5 is a graph showing a depth distribution of the abundance ratio of each element on the surface and in the interior of the carbonaceous film on the surface of the artificial bone (Example 2)

Since nitrogen is introduced during the formation of the carbonaceous thin film 10, it can be expected that nitrogen atoms constituting the amino groups 12 are present not only on the surface of the carbonaceous thin film 10 but also in the interior of the same. To confirm this, while etching the carbonaceous thin film 10 of Example 2 with an argon ion beam, the abundance ratios of calcium (Ca), phosphorus (P), oxygen (O), carbon (C), and nitrogen (N) were measured by using ESCA850M of SHIMADZU CORPORATION. FIG. 5 shows a graph showing the etching depth dependence of the abundance ratio of each element measured; namely, a depth distribution of the abundance ratio of each element on the surface and in the interior of the carbonaceous thin film 10 provided on the outer surface of the artificial bone 1 (Example 2). From FIG. 5, it can be seen that the abundance ratio of nitrogen is substantially constant from the surface of the carbonaceous thin film 10 to the depth of 100 angstroms (0.01 μm). This confirms that the amino groups 12 are provided on the surface and in the interior of the carbonaceous thin film 10. Thus, by using plasma containing nitrogen, hydrocarbon, and argon, it is possible to provide the amino groups 12 on the surface and in the interior of the carbonaceous thin film 10. Thereby, even if the surface of the carbonaceous thin film 10 is erode by the blood stream or the like, the amino groups 12 are exposed on the surface of the carbonaceous thin film 10 so that the state in which the amino groups 12 are provided on the surface of the carbonaceous thin film 10 is maintained, whereby the affinity between the artificial bone 1 and the osteogenic cells can be maintained.

In the present embodiment, since the flow rate of nitrogen is maintained constant during the film formation, the amino groups 12 are distribute substantially uniformly on the surface and in the interior of the carbonaceous thin film 10. As a result, regardless of an amount of erosion of the carbonaceous thin film 10, the affinity between the artificial bone 1 and the osteogenic cells can be maintained substantially constant.

To provide an affinity between the artificial bone 1 and the osteogenic cells, the abundance ratio of nitrogen on the surface and in the interior of the carbonaceous thin film 10 is preferably greater than or equal to 3%, and more preferably is greater than or equal to 10%. Thereby, the carbonaceous thin film 10 can be provided with sufficient amino groups 12 to provide an affinity between the artificial bone 1 and the osteogenic cells.

In the present embodiment, the abundance ratio of nitrogen is 10.2% in Example 1, 17% in Example 2, and 13% in Example 3. Therefore, the affinity between the artificial bone 1 and the osteogenic cells is improved. In Examples 1 to 3, since the abundance ratio of nitrogen is greater than or equal to 10%, the ratio of the abundance ratio of nitrogen to the abundance ratio of carbon also is greater than or equal to 10%.

Next, to confirm the effects of the provision of the carbonaceous thin film 10, an alkaline phosphatase (ALP) dyeing experiment was conducted on three samples of Comparative Example and three samples of Example 2 by using mouse osteoblast-like cells (MC3T3-E1 cell line). As shown in FIG. 6, in the ALP dyeing experiment on day 4, almost no dyeing by ALP dyeing is observed in the case of Comparative Example shown in the upper row. On the other hand, ALP dyeing is observed in each of the three samples of Example 2 shown in the lower row. Thus, it was confirmed that the provision of the carbonaceous thin film 10 promoted the proliferation and differentiation of osteoblasts and improved the affinity to the osteogenic cells.

Figure 7:
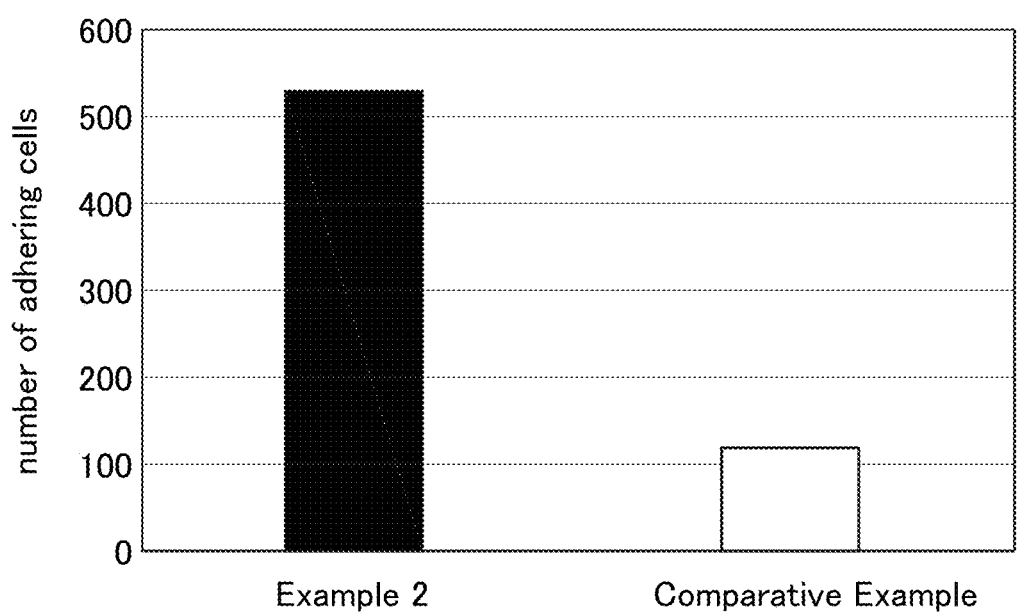
FIG. 7 is a graph showing the number of cell adhesions in a sample of the Comparative Example and the number of cell adhesions in a sample of Example 2 which were counted when two hours elapsed after liquid cell suspension culture medium was dripped into the respective samples.

Further, to confirm the effects of the provision of the carbonaceous thin film 10, an experiment was conducted to evaluate the cell adhesion by using the osteoblastic cell line, MC3T3-E1. Liquid cell suspension culture was dripped into the respective samples of Example 2 and the Comparative Example, and two hours after that, the number of cells that have adhered to each sample (the number of adhering cells) was counted. As shown in FIG. 7, the number of adhering cells is significantly increased in the sample of Example 2 compared to the sample of the Comparative Example, and this confirms the cell adhesion promoting effect of the provision of the carbonaceous thin film 10.

To confirm that the amino groups 12 are formed on the carbonaceous thin film 10 due to the introduction of nitrogen during the film formation, three samples (sample 1, sample 2, and sample 3) were prepared by conducting the film formation with only the nitrogen flow rate changed. Note that sample 1 was prepared by using a silicon wafer instead of the base material 2 and helium instead of argon, but by conducting the plasma irradiation for 30 minutes under the otherwise same plasma conditions as in Example 1. Sample 2 was prepared by subjecting a silicon wafer to the plasma irradiation for 30 minutes under the same plasma conditions as in the preparation of sample 1 except that only the flow rate of nitrogen was doubled. Sample 3 was prepared by subjecting a silicon wafer to the plasma irradiation for 30 minutes under the same plasma conditions as in the preparation of sample 1 except that only the flow rate of nitrogen was changed to zero. Note that though each of sample 1 to sample 3 was prepared by irradiating plasma onto a silicon wafer, in the case where the silicon wafer is used also, the carbonaceous thin film 10 having a composition similar to that obtained when the base material 2 is used is formed. After the film formation, XPS was measured for the carbonaceous thin film 10 formed on the surface of each of samples 1 to 3. Note that KRATOS AXIS-165X made by SHIMADZU CORPORATION was used in the measurement of XPS. With KRATOS AXIS-165X, the spot diameter of X-ray was about 2 mm.

Figure 8:
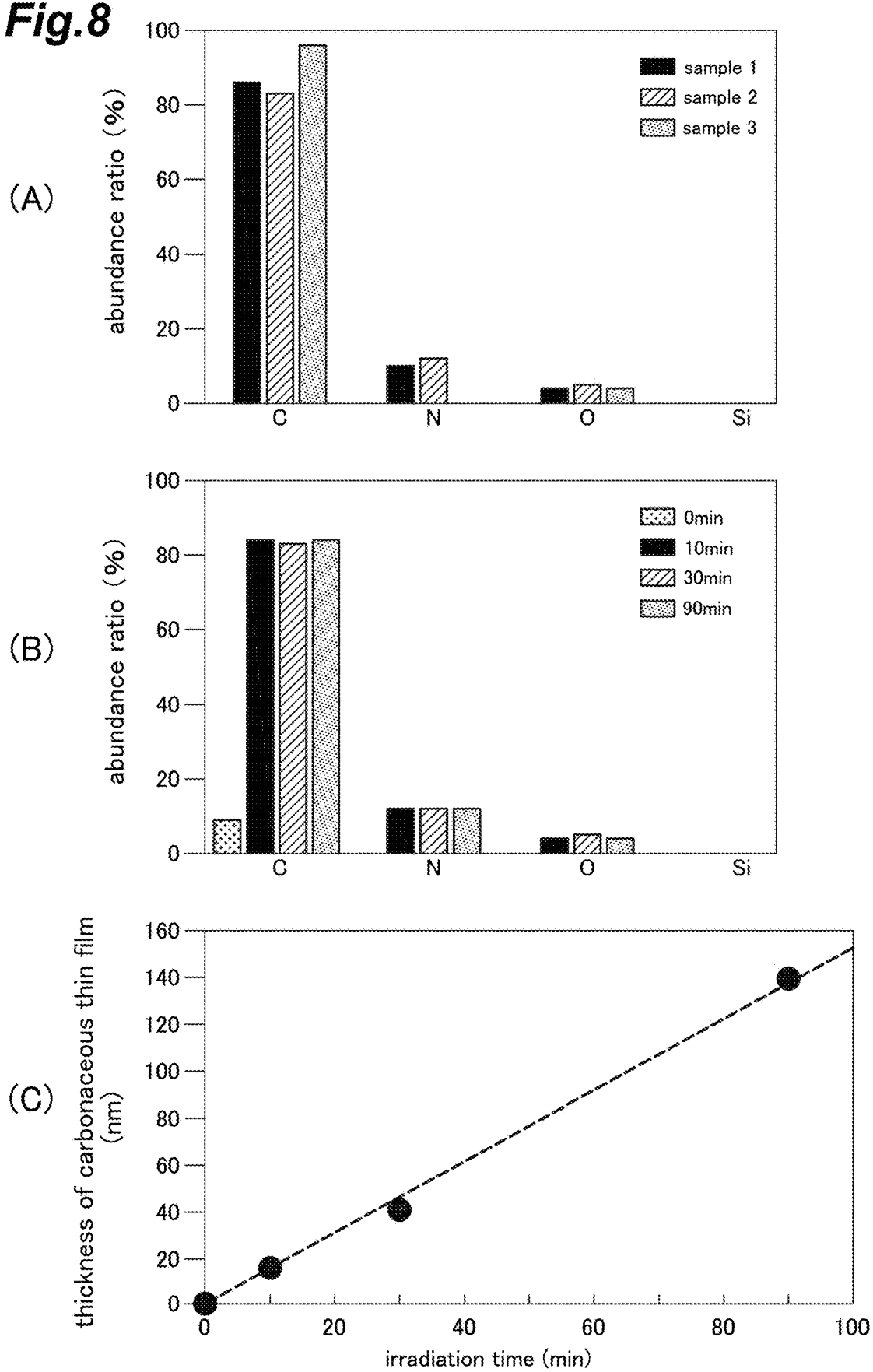
FIG. 8 includes (A) a graph showing the abundance ratios of the elements in samples 1 to 3, (B) a graph showing the abundance ratios of the elements for the plasma irradiation time of 0 minute, 10 minutes, 30 minutes, and 90 minutes, and (C) a graph showing the dependence of the thickness of the carbonaceous thin film on the plasma irradiation time.

(A) of FIG. 8 shows the abundance ratios (%) of carbon (C), nitrogen (N), oxygen (O), and silicon (Si) of samples 1 to 3 obtained based on C (carbon) is spectrum, N (nitrogen) is spectrum, O (oxygen) is spectrum, and Si (silicon) 2p spectrum of XPS. It can be confirmed that the abundance ratio of nitrogen is substantially 0% in sample 3, while the abundance ratio of nitrogen is greater than or equal to 10% in samples 1 and 2. Thus, it can be confirmed that the introduction of nitrogen during the film formation results in the abundance ratio of nitrogen having a significant value greater than 0% (for example, greater than or equal to 3%, and more clearly, greater than or equal to 10%), and as the flow rate of nitrogen increases, the abundance ratio of nitrogen increases.

Next, to further confirm that the amino groups 12 are provided in the interior of the carbonaceous thin film 10, plasma irradiation was performed on a silicon wafer under the plasma conditions used at the time of preparation of sample 1 but with varying plasma irradiation times. Thereafter, XPS was measured by using KRATOS AXIS-165X to obtain the abundance ratio of each element. (B) of FIG. 8 shows the abundance ratios (%) of carbon (C), nitrogen (N), oxygen (O), and silicon (Si) for the plasma irradiation times of 0 minute (namely, no plasma irradiation), 10 minutes, 30 minutes, and 90 minutes. Note that in the calculation of the abundance ratios, C (carbon) 1s spectrum, N (nitrogen) is spectrum, O (oxygen) 1s spectrum, and Si (silicon) 2p spectrum wee used as in (A) of FIG. 8. As shown in (B) of FIG. 8, the abundance ratio of nitrogen is about 12% and constant, and thus, it can be seen that the abundance ratio of nitrogen does not depend on the plasma irradiation time. As shown in (C) of FIG. 8, the thickness of the carbonaceous thin film 10 monotonically increases with the plasma irradiation time, and thus, it can be confirmed that in the interior of the carbonaceous thin film 10 also, nitrogen, namely, the amino groups 12 are present uniformly.

Figure 9:
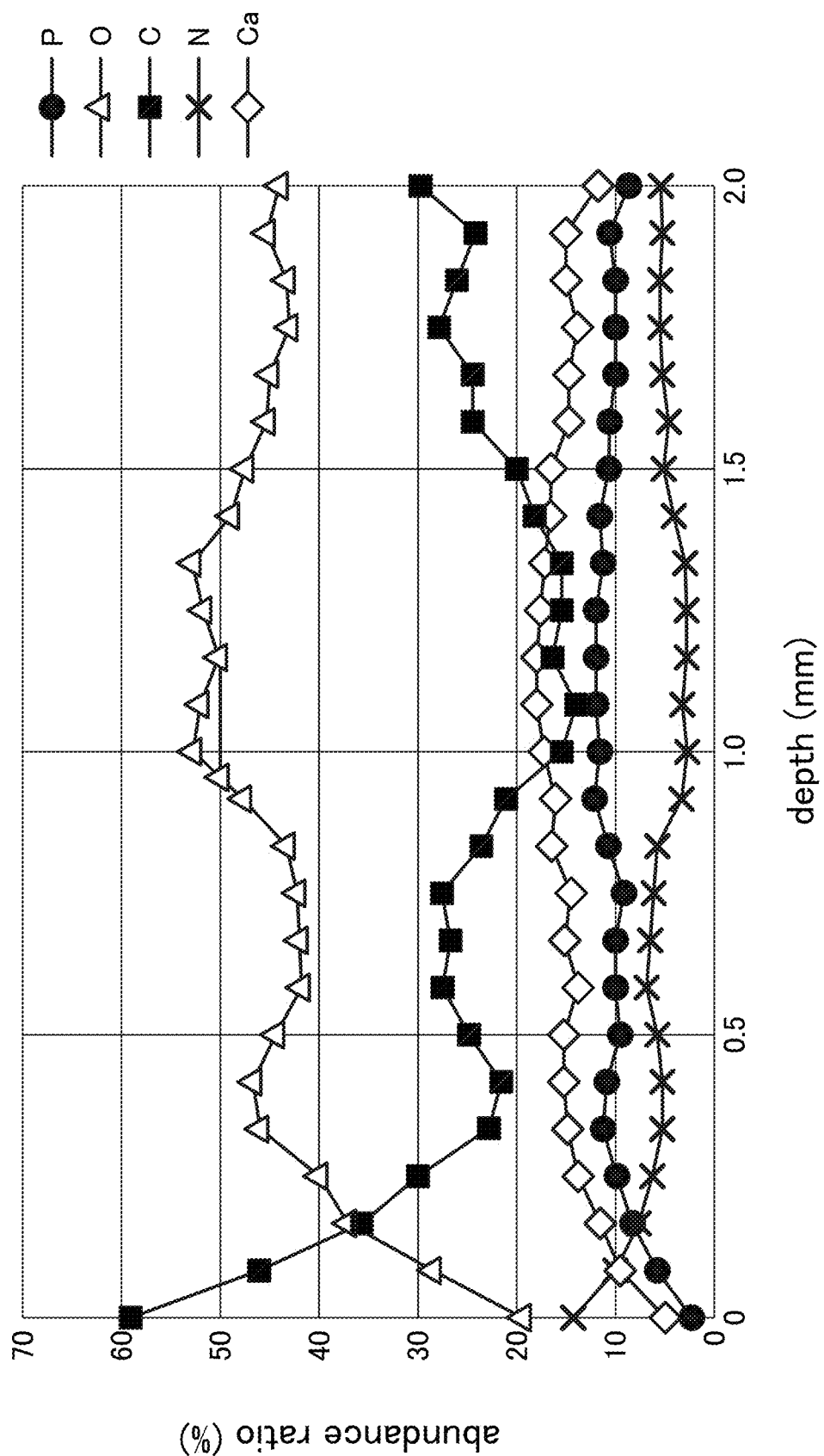
FIG. 9 is a graph showing the depth dependence of the abundance ratios of Ca (calcium), phosphorus (P), oxygen (O), carbon (C), and nitrogen (N) in the artificial bone 1 of Example 2.

Next, the depth dependence of the abundance ratios of Ca (calcium), phosphorus (P), oxygen (O), carbon (C), and nitrogen (N) of the artificial bone 1 of Example 2 was evaluated, and the graph shown in FIG. 9 was obtained. Here, the abundance ratios were determined based on the energy spectrum of photoelectrons obtained by using X-ray photoelectron spectroscopy (XPS), and the measurement was performed by using PHI Quantera SXM. Note that a reference point, which is a reference of the depth (namely, a point where the depth is zero), was determined by obtaining an approximate position of the upper end of the artificial bone 1 of Example 2 to be measured by using a camera equipped to Quantera SXM, measuring XPS randomly at multiple points in the vicinity thereof, and thereafter determining, from among the multiple points, a point where the maximum XPS signal was obtained.

As shown in FIG. 9, the abundance ratios of carbon and nitrogen are the highest on the top surface and decrease with the depth in the depth range of 0 to 0.5 mm. It can be confirmed that thereafter, in the vicinity of the bottom surface (~2 mm), the abundance ratios of carbon and nitrogen have a tendency to slightly increase. Since the abundance ratio of nitrogen decreases with the depth in the depth range of 0 to 0.5 mm and the abundance ratio of nitrogen is about 0.5% when the film forming step is not performed, it could be confirmed that as a result of the film forming step, nitrogen was present to the depth of 0.5 to 1.0 mm. Thus, it can be said that in the artificial bone 1 of Example 2, the amino groups 12 were formed to the depth of 0.5 to 1.0 mm.

Subsequently, the affinity between the artificial bone 1 and the osteoblast-like cells, which are osteogenic cells, was evaluated. First, the artificial bone 1 of Example 2 after one month from manufacture was subjected to autoclave sterilization. A liquid cell suspension containing the osteoblastic cell line, MC3T3-E1 ($3 \times 10^5$ cells/35 μl) was dripped onto the top surface of the artificial bone 1 after one day from the sterilization (see (A) of FIG. 10), and adhesion was caused to occur for about one hour (see (B) of FIG. 10). After adhesion, the artificial bone 1 was placed in a petri dish, to which a culture medium was added, and continuous culture was performed for about two hours (see (C) of FIG. 10). Thereafter, the artificial bone 1 was taken out and dyed with crystal violet. Then, the dyed artificial bone 1 was cut in the middle and the image of the section shown in (A) of FIG. 11 was obtained. Similar processing was performed on the base material 2, and the image of the section shown in (B) of FIG. 11 was obtained. Compared to (A) of FIG. 11, it can be confirmed that in (B) of FIG. 11, the interior is dyed and thus the osteogenic cells can enter the artificial bone 1 easily.

Figure 10:
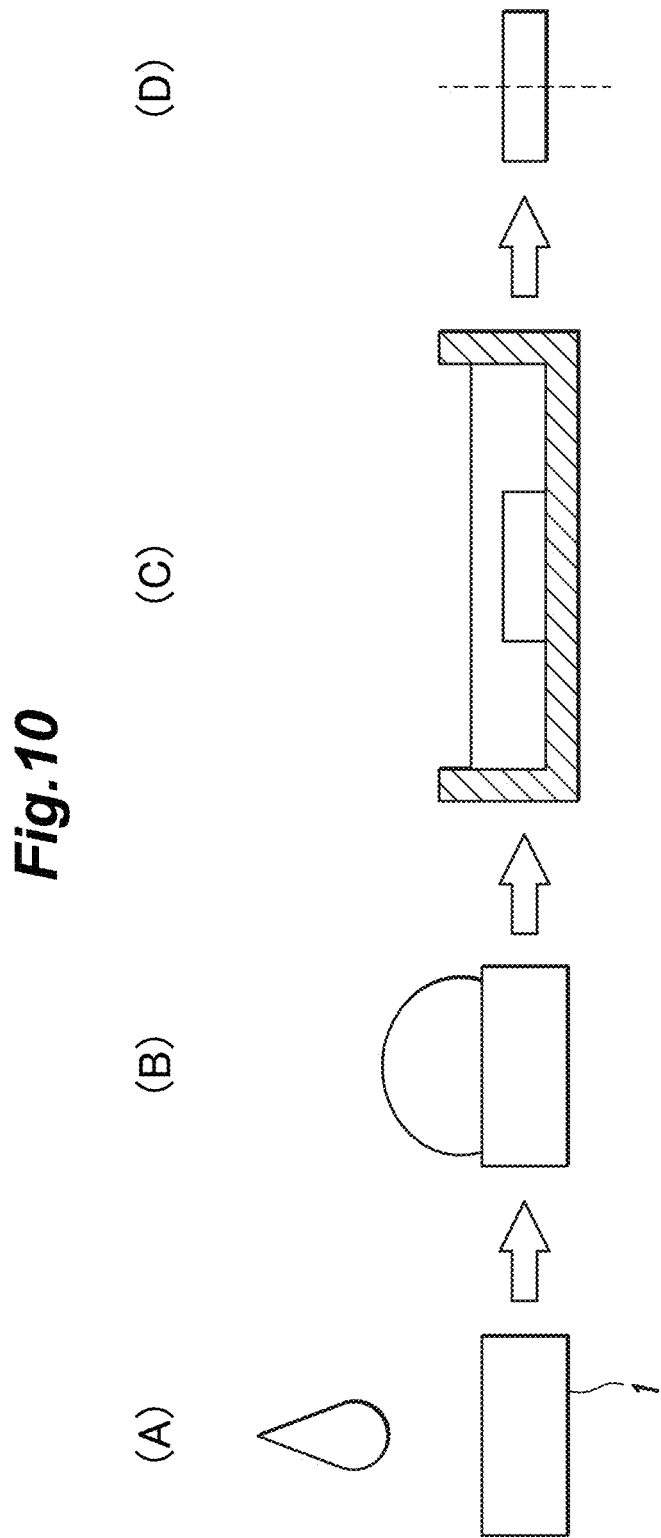
FIG. 10 is an explanatory diagram for explaining procedures (A) to (D) for evaluating the affinity between the artificial bone and the osteoblast-like cells.
Figure 12:
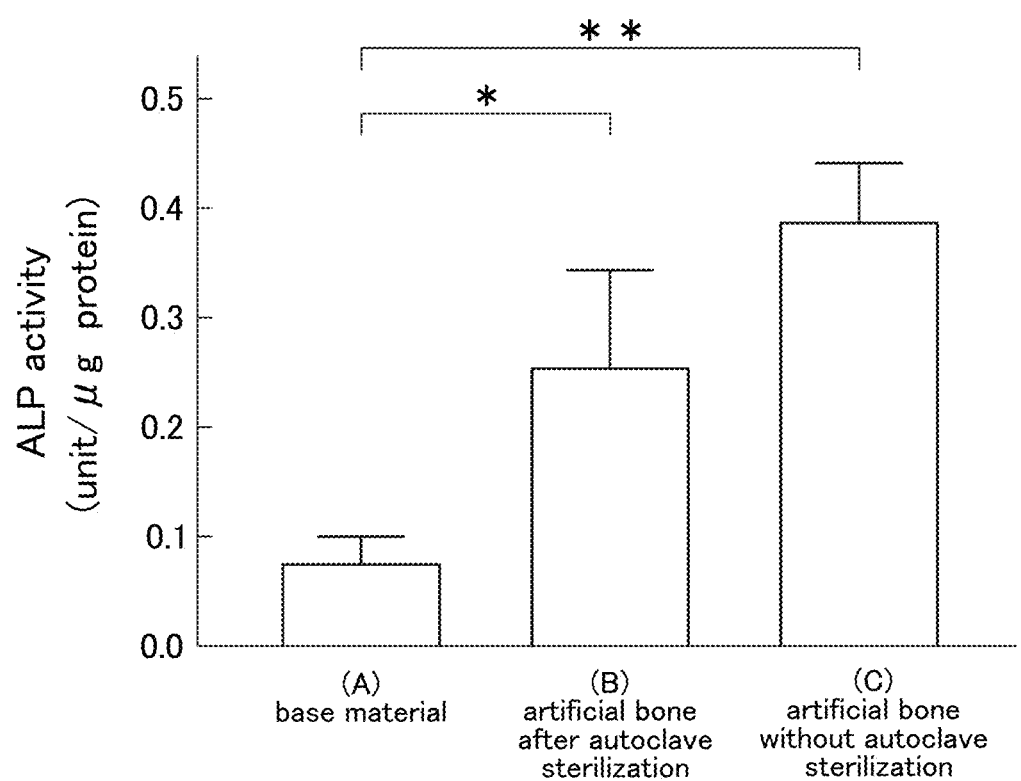
FIG. 12 is a graph showing ALP activities corresponding to (A) the base material, (B) the artificial bone after autoclave sterilization, and (C) the artificial bone without autoclave sterilization.

Further, after performing the process shown in FIG. 10 on each of the base material 2, the artificial bone 1 of Example 2 after autoclave sterilization, and the artificial bone 1 of Example 2 without autoclave sterilization, ALP activity was measured. FIG. 12 shows ALP activity values respectively measured for (A) the base material 2, (B) the artificial bone 1 of Example 2 after autoclave sterilization, and (C) the artificial bone 1 of Example 2 without autoclave sterilization. By comparing (A) and (C) of FIG. 12, it can be confirmed that the artificial bone 1 has a higher affinity to the osteogenic cells compared to the base material 2. Also, comparison between (B) and (C) of FIG. 12 shows that the affinity between the artificial bone 1 and the osteogenic cells does not decrease considerably after the autoclave sterilization treatment, which indicates that the osteogenic cells have entered the interior of the artificial bone 1.

Further, to evaluate the affinity between the artificial bone 1 and the osteogenic cells, each of the base material 2 and the artificial bone 1 of Example 2 was transplanted to a bone of a 10 week old male SD rat serving as a host after autoclave sterilization, and was X-rayed six weeks from the transplant. (A) and (B) of FIG. 13 are X-ray photographs of the base material 2, and (C) and (D) of FIG. 13 are X-ray photographs of the artificial bone 1 of Example 2. From (A) and (C) of FIG. 13 and portions of (B) and (B) of FIG. 13 surrounded by broken lines, it can be confirmed that since the osteogenic cells have entered the interior, the interior is white in the artificial bone 1 of Example 2 compared to the base material 2. Thus, it can be confirmed that compared to the base material 2, the osteogenic cells were easy to enter in the artificial bone 1.

FIG. 14 shows photographs of (A) the base material 2 after the transplant and (D) the artificial bone 1 of Example 2 after the transplant, each having been taken out from the SD rat and dyed. (B) and (C) of FIG. 14 are enlarged photographs of a central portion (the portion surrounded by a broken line in (A) of FIG. 14) and a contact portion with the bone of the rat (the portion surrounded by a one-dot chain line in (A) of FIG. 14), respectively, of the base material 2 after the transplant. (E) and (F) of FIG. 14 are enlarged photographs of a central portion (the portion surrounded by a broken line in (D) of FIG. 14) and a contact portion with the bone of the rat (the portion surrounded by a one-dot chain line in (D) of FIG. 14), respectively, of the artificial bone 1 of Example 2 after the transplant. In (B) of FIG. 14, the interior of the pores is primarily a fibrous tissue, and only a small amount of bone formation is observed. In contrast, in (E) of FIG. 14, bone formation was observed in most of the pores. Also, in (C) of FIG. 14, a fibrous tissue intervenes at the host bone interface to make a false joint, while in (F) of FIG. 14, bone fusion can be confirmed at the host bone interface.

Concrete embodiments have been described in the foregoing, but the present invention is not limited by the above-described embodiments and may be modified or altered in various ways. In the above-described embodiment, the base material 2 has a substantially rectangular parallelepiped shape, but the present invention is not limited to this, and the base material 2 may be granular, cylindrical, or columnar, for example.

In the film forming step, if there is a risk that the carboxylic groups 14 may be formed due to oxygen adsorbed on the inner wall of the chamber 21 or leakage of the chamber 21, it is preferred to keep a state in which the inert gas is flowing for about 5 to 10 minutes before applying voltage to the plate electrodes 22, 23. Thereby, the interior of the chamber 21 is ventilated by the inert gas so that the oxygen concentration is lowered, and therefore, the attachment of the carboxylic groups 14 to the carbonaceous thin film 10 becomes difficult to occur. Also, a step of replacing the interior of the chamber 21 with an inert gas (for example, argon) and evacuating the chamber 21 by using the vacuum pump 25 (purge/flush) may be repeated multiple times prior to the film forming step, thereby to lower the oxygen concentration in the interior of the chamber 21.

In the above-described embodiment, the carbonaceous thin film 10 was a polymer film, but the present invention is not limited to this, and the carbonaceous thin film 10 may be any thin film. For example, the carbonaceous thin film 10 may be made of graphite carbon or amorphous carbon.

In the above-described embodiment, the carbonaceous thin film 10 containing the functional groups 13 including the amino groups 12 on the surface and in the interior thereof was formed by the chemical vapor deposition method using the plasma containing hydrocarbon, inert gas, and nitrogen, but the present invention is not limited to this method. For example, instead of nitrogen, a gas comprising molecules containing nitrogen atoms may be used. It is also possible to use a gas comprising molecules of at least one kind selected from the group consisting of nitrogen, ammonia, and cyclopropylamine. By using the gas comprising molecules of at least one kind selected from the group consisting of nitrogen, ammonia, and cyclopropylamine, it is possible to more reliably provide the amino groups 12 on the surface and in the interior of the carbonaceous thin film 10.

In the above-described embodiment, methane was used as hydrocarbon, but the present invention is not limited to this embodiment and hydrocarbon may be ethane, propane, or ethylene, for example.

In the above-described embodiment, the affinity between the artificial bone 1 and the osteogenic cells was evaluated based on the abundance ratio of nitrogen on the surface and in the interior of the carbonaceous thin film 10 (the abundance ratio of nitrogen in the carbonaceous thin film 10 containing carbon, oxygen, etc.), but the present invention is not limited to this embodiment. For example, the evaluation may be performed based on the ratio of the abundance ratio of nitrogen to the abundance ratio of carbon on the surface and in the interior of the carbonaceous thin film 10, and in this case, the abundance ratio of nitrogen on the surface and in the interior of the carbonaceous thin film 10 preferably is at least 10% of the abundance ratio of carbon.

Glossary

1: artificial bone
2: base material

6: pore
7: pore wall surface
8: interpore connecting portion
10: carbonaceous thin film
12: amino group
13: functional group

The invention claimed is:

1. An artificial bone comprising:
a base material containing porous ceramics provided with mutually interconnected pores;
a carbonaceous thin film formed by plasma CVD or CVD in general using nitrogen, hydrocarbon and inert gas on an outer surface of the base material and wall surfaces of the pores; and
functional groups including amino groups provided over the entire thickness of the film on a surface and in an interior of the carbonaceous thin film.

2. The artificial bone according to claim 1, wherein an abundance ratio of nitrogen on the surface and in the interior of the carbonaceous thin film is at least 3%.

3. The artificial bone according to claim 2, wherein the abundance ratio of nitrogen on the surface and in the interior of the carbonaceous thin film is at least 10%.

4. The artificial bone according to claim 1, wherein the pores are substantially spherical in shape and have an average diameter greater than or equal to 50 μm and less than or equal to 600 μm, and interpore connecting portions each interconnecting two pores with each other are substantially circular in shape and have an average diameter greater than or equal to 5 μm.

5. The artificial bone according to claim 1, wherein the carbonaceous thin film is formed to reach the wall surfaces of the pores at a depth of 1 mm or more from the outer surface of the base material.

6. The artificial bone according to claim 1, wherein the carbonaceous thin film is formed to reach the wall surfaces of the pores positioned in a central part of the base material.

7. The artificial bone according to claim 1, wherein the carbonaceous thin film is a polymer film.

8. A manufacturing method of an artificial bone, the method comprising:
preparing a base material containing porous ceramics provided with mutually interconnected pores; and
forming a carbonaceous thin film on an outer surface of the base material and on wall surfaces of the pores by a chemical vapor deposition method using plasma containing hydrocarbon, molecules containing nitrogen atoms, and an inert gas; wherein the carbonaceous thin film contains functional groups including amino groups provided over the entire thickness of the film on a surface and in an interior of the carbonaceous thin film.

* * * * *